United States Patent
Randall

(10) Patent No.: US 8,753,118 B2
(45) Date of Patent: Jun. 17, 2014

(54) DENTAL BRIDGE

(76) Inventor: James Michael Randall, Overland Park, KS (US)

(*) Notice: Subject to any disclaimer, the term of this patent is extended or adjusted under 35 U.S.C. 154(b) by 563 days.

(21) Appl. No.: 12/245,434

(22) Filed: Oct. 3, 2008

(65) Prior Publication Data

US 2010/0086895 A1 Apr. 8, 2010

(51) Int. Cl.
  *A61C 13/12* (2006.01)
  *A61C 13/225* (2006.01)

(52) U.S. Cl.
  USPC ............................ 433/181; 433/183

(58) Field of Classification Search
  USPC ................. 433/174, 180–183, 190–195
  See application file for complete search history.

(56) References Cited

U.S. PATENT DOCUMENTS

| | | | |
|---|---|---|---|
| 2,836,891 A | 6/1958 | Schubert | |
| 3,613,244 A | 10/1971 | Flecher | |
| 4,193,194 A | 3/1980 | Dalise | |
| 4,362,509 A | 12/1982 | Sulc | |
| 4,400,157 A * | 8/1983 | Moore | 433/31 |
| 4,474,499 A | 10/1984 | Pedrazzini | |
| 4,475,891 A * | 10/1984 | Hader | 433/181 |
| 4,540,367 A | 9/1985 | Sulc | |
| 4,731,020 A | 3/1988 | Kawahara et al. | |
| 4,738,622 A | 4/1988 | Kawahara et al. | |
| 4,744,757 A * | 5/1988 | Adair et al. | 433/180 |
| 4,789,338 A | 12/1988 | Eisenmann | |
| 4,797,099 A | 1/1989 | Poveromo | |
| 4,813,873 A | 3/1989 | Seaton | |
| 5,174,755 A | 12/1992 | Fukuda | |
| 5,453,007 A | 9/1995 | Wagher | |
| 5,885,077 A | 3/1999 | Jeffer | |
| 2002/0142265 A1 | 10/2002 | Weissman | |
| 2006/0127834 A1 * | 6/2006 | Szwajkowski et al. | 433/2 |
| 2007/0254265 A1 * | 11/2007 | Callan | 433/174 |
| 2007/0259315 A1 | 11/2007 | Last-Pollak | |
| 2009/0029320 A1 * | 1/2009 | Auderset et al. | 433/182 |

FOREIGN PATENT DOCUMENTS

WO WO2006105684 * 10/2006 ........... A61C 13/265

OTHER PUBLICATIONS

Herbert T. Shillingburg, Jr., Sumiya Hobo, Lowell D. Whitsett; "Non-rigid Connectors"; *Fundamentals of Fixed Prosthodontics*, 3rd Edition; 1997; pp. 531-532; Quintessence Publishing Co., Inc.; Carol Stream, Illinois, USA.

* cited by examiner

*Primary Examiner* — Eric Rosen
(74) *Attorney, Agent, or Firm* — Stinson Leonard Street LLP

(57) ABSTRACT

A system for attaching a natural tooth to a dental implant. The system includes a dental prosthesis and an elastomeric cushion. The dental prosthesis has a first end and a second end. The first end is fixed to a natural tooth and the second end is engaged with a dental implant. The elastomeric cushion is positioned in contact, either directly or indirectly, with at least a portion of the dental implant and at least a portion of the dental prosthesis such that the elastomeric cushion permits movement of the second end relative to the dental implant in response to movement of the natural tooth transferred through the dental prosthesis to the second end.

19 Claims, 4 Drawing Sheets

DENTAL BRIDGE

CROSS-REFERENCE TO RELATED APPLICATIONS

Not Applicable.

STATEMENT REGARDING FEDERALLY SPONSORED RESEARCH OR DEVELOPMENT

Not applicable.

BACKGROUND OF THE INVENTION

1. Field of the Invention

The present invention is directed to the field of dentistry, and is more specifically directed to a dental bridge system that may be secured between a natural tooth and an implant in such a manner so as to permit limited movement of the natural tooth and implant relative to one another.

2. Description of Related Art

Many patients require dental restorations or prostheses or a combination of dental restorations and prostheses to restore function or for aesthetic reasons. Some common dental restorations and prostheses include inlays, onlays, veneers, implants, crowns, bridges, and dentures. Depending on the patient's need, the dental restorations and prostheses can be removable or fixed. Dental restorations or dental prostheses provide the appearance of teeth and are constructed to mimic the function of teeth, such as masticating food and allowing for proper speech patterns.

One type of fixed or permanent dental restoration is an implant. Implants can replace an individual tooth or a combination of teeth and can support a crown, a bridge, or a denture. The implant functions as an artificial tooth root. The most common type of implant is secured in the bony tissue of the upper or lower jaw. Implants can also be secured on top of the jaw bone under the periosteum. Implants secured in the bony tissue of the upper or lower jaw are generally made out of titanium, titanium alloy, or some other medically compatible metal. A portion of the implant is screwed or tapped into a surgically prepared site in the bony tissue of the upper or lower jaw. The portion of the implant left exposed above the gumline can support a prosthesis such as a crown, a bridge, or a denture. Once the implant is in place, a process called osseointegration occurs. Osseointegration is when the bony tissue grows around the portion of the implant inserted in the jaw such that there is a structural and functional connection between the living bony tissue and the surface of the dental implant. After osseointegration has occurred, the portion of the implant inserted into the jaw is rigidly fixed in place by the bony tissue. The prosthesis can either be more or less permanently fixed to the implant or can be secured such that it is regularly removable.

Another type of dental restoration is a bridge. Bridges can be used to reduce the risk of gum disease, correct certain bite issues, improve speech, and replace missing teeth. Dental bridges are generally made up of at least two crowns. Crowns, also known as dental caps or tooth caps, are designed to cap the portion of a natural tooth at and above the gumline. Crowns essentially become the new visible portion of the tooth that can be used for chewing and allow for proper speech patterns. Crowns can also be made to fit over the portion of a dental implant left exposed above the gumline as described above. Crowns are generally made out of porcelain or dental ceramic, metal such as gold or other metal alloy, or a combination of porcelain and metal. Typically, dental bridges also have at least one artificial tooth, or pontic, fused between the two dental crowns.

Bridges containing pontics are a useful dental restoration option when multiple implants to restore multiple teeth cannot be used due to certain anatomical limitations or as a more cost effective treatment option. For example, when a patient loses a tooth in the lower jaw and the use of an implant would require inserting the implant in the lower jaw near the inferior alveolar nerve, there is a risk that inserting the implant could injure the nerve. If the missing tooth location is between two natural teeth or is between two dental implants, then a traditional dental bridge having a pontic can be used to restore the patient's missing teeth.

Another example of how bridges can be a particularly useful method of restoration is when the patient loses a tooth in the upper jaw below a sinus. As the bone where the missing tooth deteriorates through non-use, the sinus cavity expands into the space left by the bone, creating a pneumatized sinus. Normally, inserting an implant where there is a pneumatized sinus requires a sinus grafting procedure where the floor of the sinus is lifted by placing a bone graft, thereby creating adequate bony tissue to support the implant. This procedure is expensive and requires a six to twelve month recovery period. If the missing tooth space has a natural tooth on each side or a dental implant on each side, then a traditional dental bridge having a pontic can be used instead of an implant, thereby avoiding the sinus grafting procedure.

A traditional dental bridge cannot be anchored to both a natural tooth and an implant without significant risk. This is because natural teeth and dental implants respond differently to occlusal or compressive forces. The root of a natural tooth rests in a socket in the bony tissue of the jaw where it is attached and cushioned with periodontal ligament fibers. These fibers allow the natural tooth to move slightly in response to occlusal forces. The space between the tooth root and a wall of the bony tissue socket is roughly 0.25 mm. Normal, healthy physiologic lateral tooth mobility can range from less than 0.25 mm to more than 1 mm. After osseointegration, a dental implant is rigid relative to the bony tissue and cannot move in response to occlusal forces. A bridge anchored to a natural tooth on one side and to a dental implant on the other side is subjected to non-uniform stress during chewing and biting. This non-uniform stress can cause a structural failure on either end of the bridge.

BRIEF SUMMARY OF THE INVENTION

The present invention is directed to a dental bridge system that may be secured between a natural tooth and a dental implant. The system comprises a dental prosthesis and an elastomeric cushion. The dental prosthesis connects a natural tooth and a dental implant. The elastomeric cushion is positioned so that it is in contact, either directly or indirectly, with at least a portion of the dental prosthesis and at least a portion of the dental implant so as to permit movement of the dental prosthesis relative to the dental implant. As the end of the dental prosthesis that is fixed to the natural tooth moves in response to movement of the natural tooth, the end of the dental prosthesis engaging the dental implant moves against the elastomeric cushion even though the dental implant remains rigid.

It is believed that this system will be particularly effective in allowing dental bridges to be more or less permanently installed between a natural tooth and a dental implant with much less risk of structural damage to all members of the system. The elastomeric cushion allows the end of the prosthesis engaging the dental implant to move in a way that mimics the way the end of the prosthesis fixed to the natural tooth moves in response to the natural tooth movement permitted by the periodontal ligament fibers. To do this, the elastomeric cushion must be manufactured from a material that is sufficiently durable and yet is elastic enough to allow the appropriate amount of movement.

In one embodiment, the system comprises a dental prosthesis having a key formed at one end, a corresponding notch formed in a dental implant crown, and an elastomeric cushion positioned at the interface of the key and the notch The key is configured to securely fit within the notch so as to connect the prosthesis to the implant. The elastomeric cushion is positioned at the interface of the key and notch so as to permit movement of the prosthesis relative to the implant.

In an alternative embodiment the system comprises a dental prosthesis having a key formed at one end, a pocket extending outwardly from the dental implant crown, and an elastomeric cushion positioned at the interface of the key and the pocket. The key is configured to be received within the pocket so as to connect the prosthesis to the implant. The elastomeric cushion is positioned within the pocket at the interface of the key and pocket surfaces so as to permit movement of the prosthesis relative to the implant.

In another embodiment, the system comprises a dental prosthesis, having a first end configured to receive a natural tooth and a second end configured to receive the exposed portion of the dental implant, and an elastomeric cushion at the interface of the dental implant and the dental prosthesis. When positioned in place, the prosthesis connects the natural tooth to the implant. The elastomeric cushion fixed at the interface of the prosthesis and the implant enables the prosthesis to move with respect to the implant.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

Figure 1:
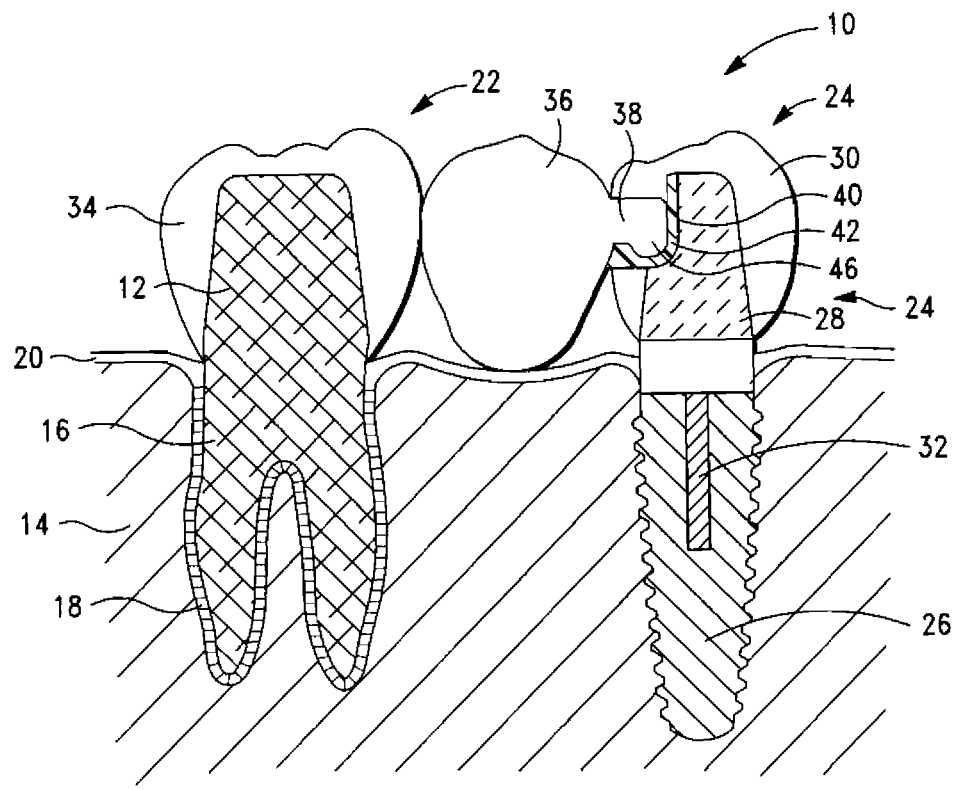
FIG. 1 is a cross-sectional view, taken along line 1 of FIG. 2, of a dental restoration having a dental bridge system in accordance with a first embodiment of the present invention.
Figure 2:
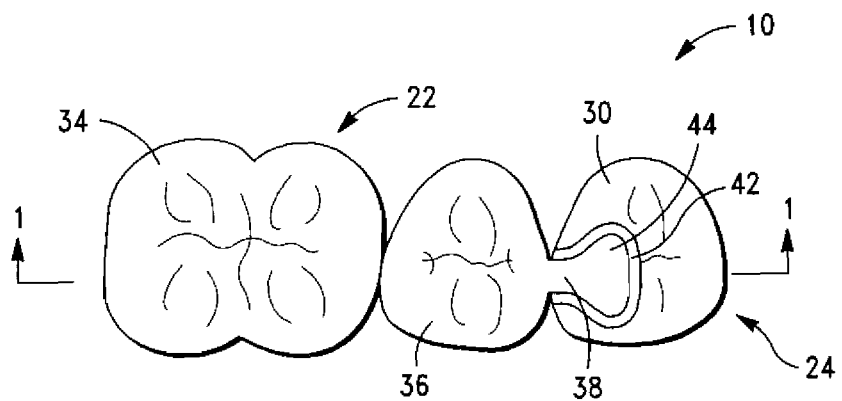
FIG. 2 is a top view of the dental bridge system of FIG. 1.

A dental bridge system for attaching a natural tooth to a dental implant according to a first embodiment of the present invention is illustrated in FIGS. 1 through 4 and generally designated with the numeral 10. As shown in FIG. 1, natural tooth 12 is embedded in bony tissue 14 via root 16. Root 16 is surrounded by periodontal ligament fibers 18 that flexibly connect root 16 to bony tissue 14. The portion of natural tooth 12 exposed above gumline 20 is prepared and shaped to support dental prosthesis 22 as discussed more fully hereinafter. When natural tooth 12 is subjected to forces, such as occlusal forces during biting and chewing, periodontal ligament fibers 18 allow root 16 and natural tooth 12 to move slightly within bony tissue 14 in response. This movement can range from less than 0.25 mm to more than 1 mm.

Figure 3:
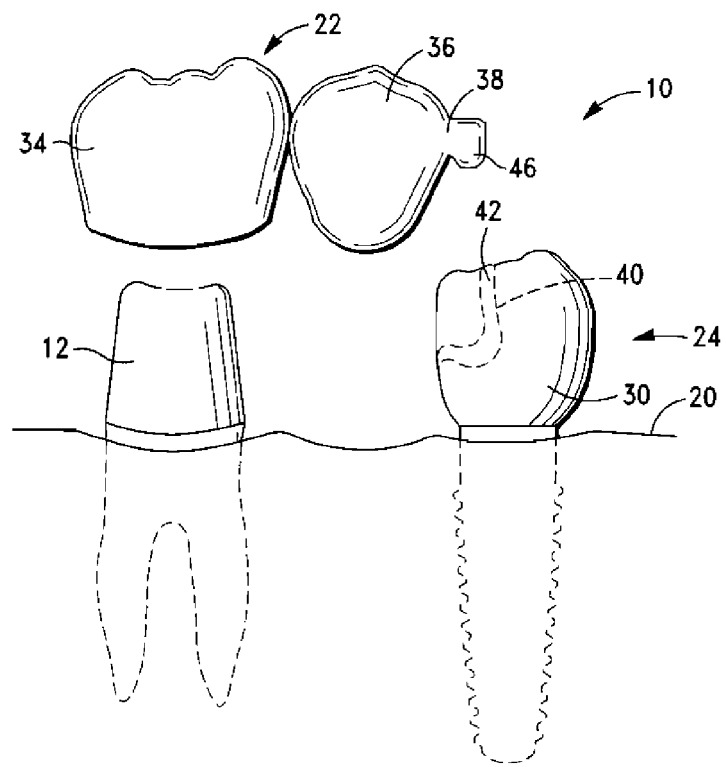
FIG. 3 is an exploded, side view of the dental restoration having the dental bridge system of FIG. 1 wherein the elastomeric cushion is fixed to the notch.

Dental implant 24 comprises implant anchor 26, exposed portion 28, and implant crown 30. Implant anchor 26 is surgically inserted into a prepared site in bony tissue 14 of the patient's upper or lower jaw. As shown in FIG. 1, exposed portion 28 is secured to implant anchor 26 via screw 32 and remains above gumline 20 after implant anchor 26 is rigidly fixed in bony tissue 14 through osseointegration. Alternatively, exposed portion 28 may be cemented or otherwise rigidly fixed to anchor 26. Implant anchor 26 functions as an artificial tooth root after osseointegration is complete. Exposed portion 28 of dental implant 24 can support a wide range of dental restoration devices and prostheses. In this embodiment, exposed portion 28 of dental implant 24 supports implant crown 30. Implant crown 30 is a cap-like structure that is permanently fixed over exposed portion 28 of dental implant 24 using dental cement or any other method known in the art. When in place, implant crown 30 functions like an artificial tooth. Notch 40 forms an opening extending into the body of implant crown 30 through a portion of the top and a side of implant crown 30. As shown in FIG. 3, an elastomeric cushion 42 is secured to the inner side and bottom surface of notch 40. As shown in FIG. 1, a corresponding notch may be formed in exposed portion 28 of dental implant 24 such that notch 40 in implant crown 30 may be seated within the notch formed within exposed portion 28.

Dental bridge system 10 comprises a dental prosthesis 22 configured to extend between and connect natural tooth 12 to dental implant 24. In this embodiment, dental prosthesis 22 comprises natural tooth crown 34, pontic 36, and key 38 extending adjacent one another along a horizontal plane generally parallel to the dental arch of the patient. Natural tooth crown 34, positioned at one end of dental prosthesis 22, forms a cap-like structure that is semi-permanently fixed to natural tooth 12 using dental cement or any other method known in the art and covers natural tooth 12. For purposes of this application, semi-permanent means affixed for long-term attachment and not designed for daily removal like dentures are, but could be removed with considerable care and effort for purposes of repair or adjustment. Pontic 36, positioned between natural tooth crown 34 and key 38, functions as an artificial tooth. Pontic 36 is generally not embedded in bony tissue 14 and sits on or above gumline 20, as shown in FIG. 1. While dental prosthesis 22 is shown in this embodiment to include a single pontic, it should be understood that multiple pontics or no pontic may be included within the prosthesis without departing from the scope of this invention. Key 38, positioned at the other end of dental prosthesis 22, has a bulbous shoulder 44 (shown in FIG. 2) extending outwardly from the upper side edge of pontic 36 along the horizontal plane parallel to the dental arch with an arm 46 (shown in FIG. 1) extending downwardly along a vertical plane perpendicular to the dental arch. Of course those practicing in the art will understand that key 38 can have a variety of different configurations without departing from the scope of the present invention. For example, key 38 may have a bulbous end and no arm or may be formed in the shape of a hook or have a t-shaped or flanged end. In the embodiment shown in FIG. 4, elastomeric cushion 42 is secured to the exposed side and bottom surface of key 38.

In the embodiment shown in FIGS. 1 through 4, dental prosthesis 22 may be molded as a single, contiguous, solid piece of dental material such as dental metal including metal alloys, or a non-metallic dental material including porcelain, zirconium oxide, or any of the numerous organic, synthetic, or processed plastic materials that are molded, cast, extruded or drawn into objects. Alternatively, dental prosthesis 22 may be formed by securing the individual components to one another by way of soldering or any other method known in the art. Each individual component can be made from the same or different dental materials.

In an alternative embodiment, dental prosthesis 22 may be formed of a core (not shown) covered by a dental material such as porcelain. The core provides a structural framework for dental prosthesis 22 and is preferably made of a suitable material such as a dental metal or can be constructed of metallic or carbon strands to create a mesh support structure. While the entirety of dental prosthesis 22 may be formed of a structural core covered with a dental material, it is also anticipated that dental prosthesis 22 may only have a structural core in certain portions, such as to support natural tooth crown 34 or pontic 36. The remainder of dental prosthesis 22 can be made from the dental material forming the covering or may be made as separate components secured to one another.

In use, dental prosthesis 22 is semi-permanently secured in place to connect natural tooth 12 to implant 24 by securing natural tooth crown 34 over natural tooth 12 and inserting key 38 into notch 40. In the embodiment shown in FIGS. 1 through 4, the exposed side and bottom surfaces of key 38 are positioned in abutting engagement with the inner side and bottom surfaces of notch 40 with elastomeric cushion 42 positioned at the interface of, and in contact with, these surfaces. Key 38 and notch 40 are configured such that key 38 remains seated in notch 40 for permanently attaching dental prosthesis 22 to implant 24. The upper exposed surface of key 38 parallel to the biting surface of implant crown 30 may be covered with porcelain or other neutral-colored material for aesthetic or hygienic reasons.

Elastomeric cushion 42 can be made from any medically acceptable load-absorbing or energy-absorbing material that allows key 38 to move relative to notch 40 in response to natural tooth movement. The material for and shape of elastomeric cushion 42 can vary depending on the desired range of movement. Elastomeric cushion 42 may be made from a combination of materials and may also have layers or zones of different materials. The materials in the zones or layers of elastomeric cushion 42 may have different compression rates or elasticity properties. One advantage of using an elastomeric cushion with zones or layers of materials having distinct properties is the ability to accommodate unusual or abnormal natural tooth movement. For example, if a natural tooth moves a significant amount in response to occlusal forces, elastomeric cushion 42 might be made of a first layer of material positioned in contact with dental implant 24 that is highly elastic and compressible and a second layer positioned in contact with dental prosthesis 22 that is less elastic and compressible. This type of elastomeric cushion could accommodate more initial movement of dental prosthesis 22 in response to the natural tooth movement but curb the movement as dental prosthesis 22 approaches dental implant 24. Similarly, elastomeric cushion 42 might have a zone of material in a central core that is stiffer or more elastic than the surrounding material to allow dental prosthesis 22 to mimic the natural tooth movement.

Elastomeric cushion 42 is formed of material to provide a range of movement that is anticipated for the specific patient by taking into consideration the anticipated range of movement of the natural tooth, and it will preferably provide a range of movement between about 0.1 mm and about 2.5 mm. One skilled in the art could use tools, such as the Miller Index or a paradontometer, to measure and assess the anticipated range of movement for the natural tooth when selecting the materials, shape, and size of elastomeric cushion 42. Examples of suitable materials include but are not limited to rubber, silicone, nylon, polyethylene, copolymers, plastic, Teflon® (commercially available from Dupont E.I. Nemours at 1007 Market Street Wilmington, Del. 19898), compomers, elastomers, santoprene, high density polyethylene, cross-linked polyethylene, polyoxymethelene, other biocompatible materials, and combinations thereof.

Figure 4:
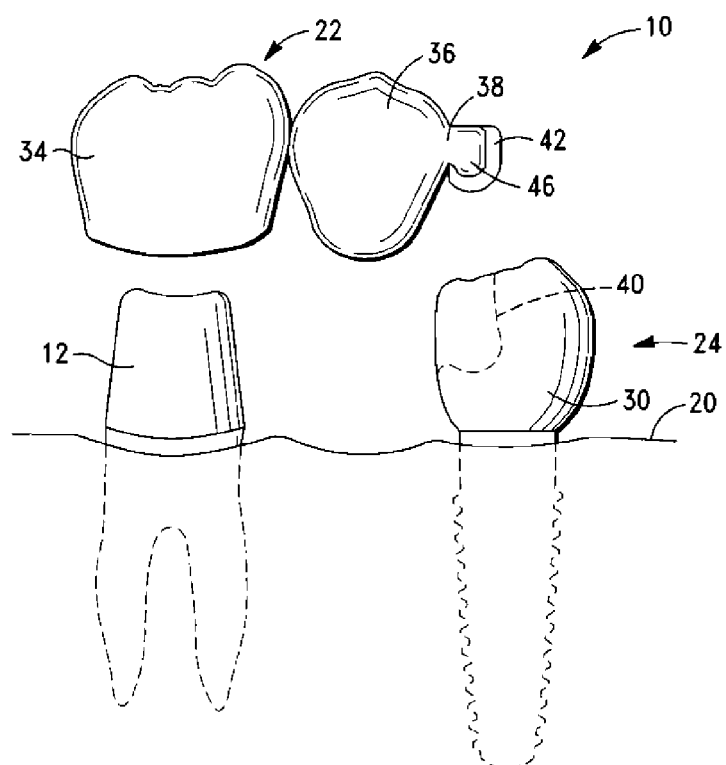
FIG. 4 is an exploded, side view of the dental restoration having the dental bridge system of FIG. 1 wherein the elastomeric cushion is fixed to the key.

In the embodiment shown in FIGS. 1, 3, and 4, elastomeric cushion 42 is shaped to fit within notch 40. As shown in FIG. 3, elastomeric cushion 42 may be fixed in notch 40 or shaped such that it is held in place in notch 40 by an interference fit (not shown). An example of such an interference fit may entail notch 40 having a wide gulley and narrow neck and elastomeric cushion 42 having a bulbous end that fits within the wide gulley of notch 40 but once in place cannot pass through the narrow neck of notch 40. Alternatively, elastomeric cushion 42 may be cemented to key 38 as shown in FIG. 4. The thickness and overall shape of elastomeric cushion 42 can vary to accommodate the desired amount of movement to be permitted and whether it is being held in place by an interference fit.

Figure 5:
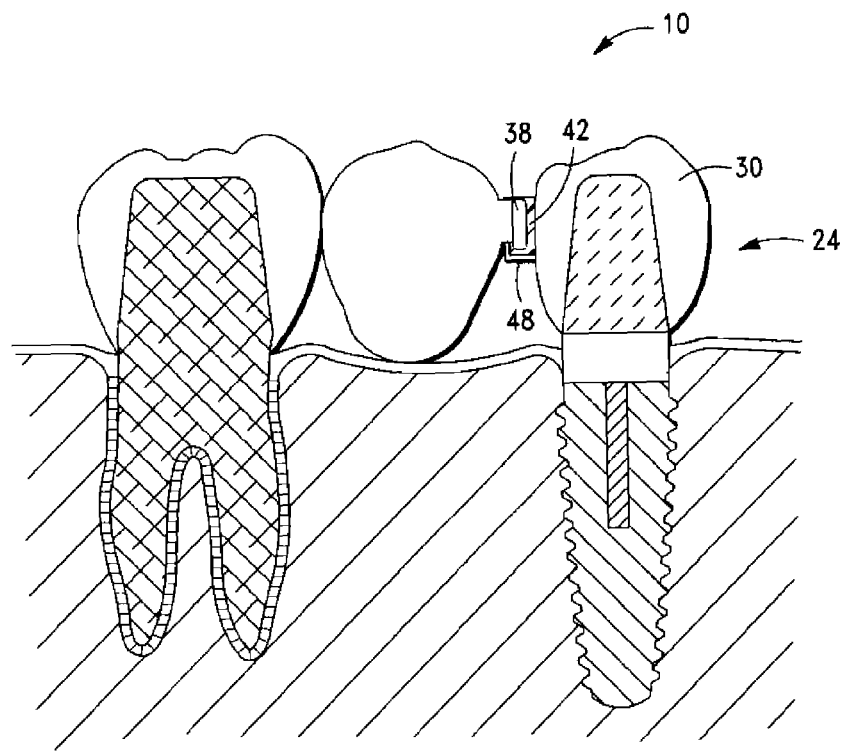
FIG. 5 is a cross-sectional view of a dental restoration having a dental bridge system in accordance with a second embodiment of the present invention.
Figure 6:
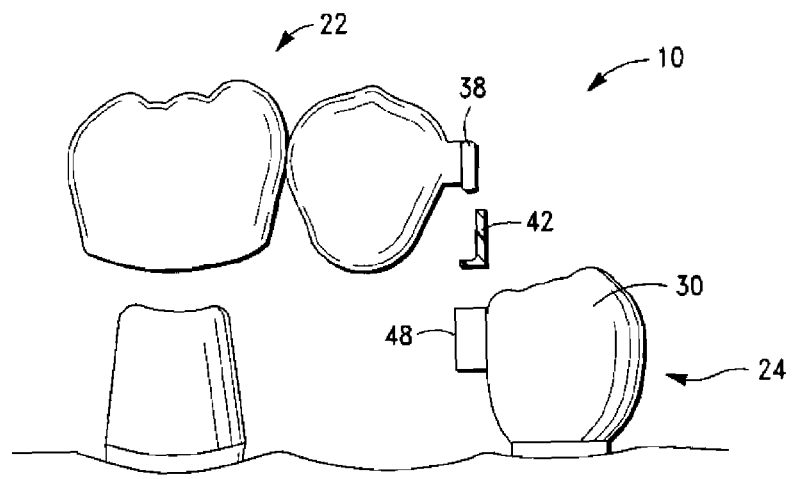
FIG. 6 is an exploded, side view of the dental restoration having the dental bridge system of FIG. 5.

In an alternative embodiment, as shown in FIGS. 5 and 6, system 10 is identical to that described heretofore with respect to FIGS. 1-4 except that key 38 is configured to be seated in key pocket 48 instead of notch 40. Dental implant 24 does not include notch 40, but instead includes key pocket 48. Key pocket 48 is permanently fixed or formed integrally with the outer surface of implant crown 30 using dental cement or any other method known in the art. Like notch 40, key pocket 48 can have a variable depth and width so as to accommodate key 38 and elastomeric cushion 42 when system 10 is fully installed. Key pocket 48 can be made from dental material such as dental metal including metal alloys, or a non-metallic dental material including porcelain, zirconium oxide, or any of the numerous organic, synthetic, or processed plastic materials that are molded, cast, extruded or drawn into objects.

Figure 7:
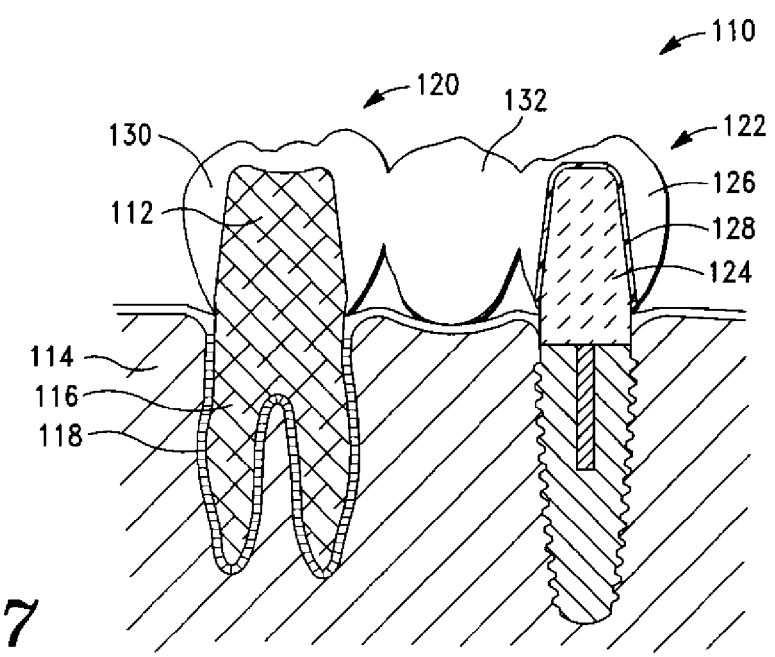
FIG. 7 is a cross-sectional view of a dental restoration having a dental bridge system in accordance with a third embodiment of the present invention.
Figure 8:
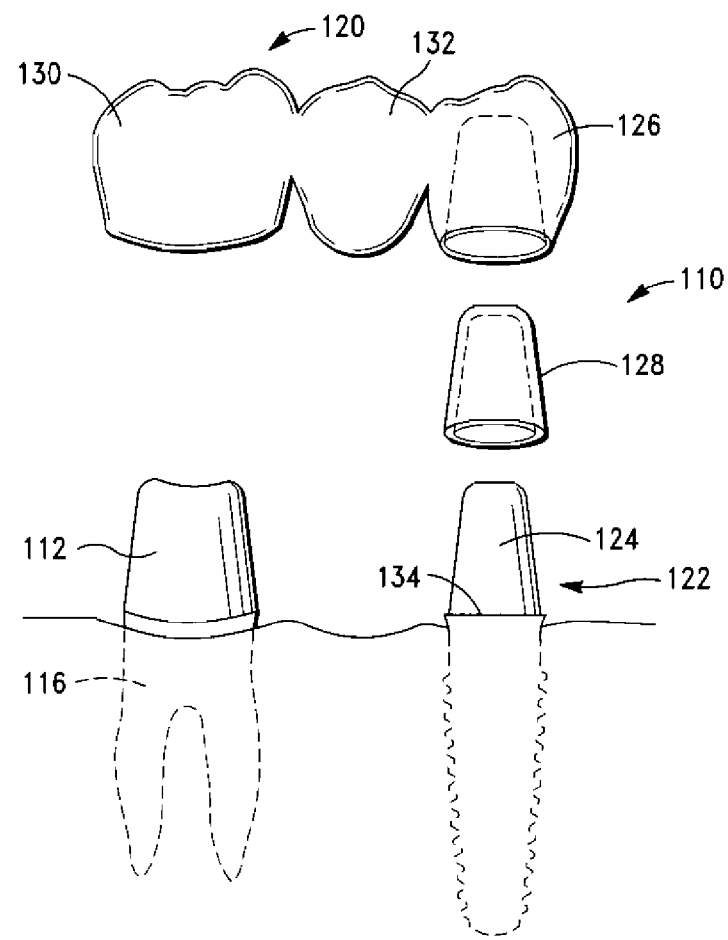
FIG. 8 is an exploded, side view of the dental restoration having the dental bridge system of FIG. 7.

A dental bridge system for attaching a natural tooth to a dental implant according to a third embodiment of the present invention is illustrated in FIGS. 7 and 8 and is generally designated with the numeral 110. Similar to the prior embodiments, natural tooth 112 is embedded in bony tissue 114 via root 116. Root 116 is surrounded by periodontal ligament fibers 118 that flexibly connect root 116 to bony tissue 114. A portion of natural tooth 112 is shaped to support dental prosthesis 120. Dental implant 122 is surgically inserted into a prepared site in bony tissue 114. As described with respect to the first embodiment above, exposed portion 124 is attached to dental implant 122 and is shaped to support dental prosthesis 120. In this embodiment, implant crown 126 is formed as a part of dental prosthesis 120, as opposed to dental implant 122. Implant crown 126 is configured to cap or otherwise engage exposed portion 124 of dental implant 122 and elastomeric cushion 128.

As shown in FIGS. 7 and 8, system 110 comprises dental prosthesis 120 and elastomeric cushion 128. Dental prosthesis 120 comprises natural tooth crown 130, pontic 132, and implant crown 126 formed together as an integral unit. Dental prosthesis 120 may be manufactured in a dental laboratory and molded as a single piece or may be made of separate components fixed together. In addition, as discussed in relation to the first embodiment, dental prosthesis 120 may comprise a structural core covered by a dental material or may comprise a solid piece of dental material.

Elastomeric cushion 128 can be formed in the shape of a cap, a donut, a c-shape, a disc, or any other shape that will permit movement between dental prosthesis 120 and exposed portion 124 of dental implant 122. Elastomeric cushion 128 can be cemented in implant crown 126 or can be cemented or otherwise permanently or removably fixed onto exposed portion 124 of dental implant 122. As shown in FIG. 8, elastomeric cushion 128 may be positioned such that when it is in place, it is seated in or on a portion of dental implant 122 that forms peripheral channel or lip 134. Elastomeric cushion 128 can be made from any medically acceptable load-absorbing or energy-absorbing material that allows dental prosthesis 120 to move relative to exposed portion 124 of dental implant 122 in response to natural tooth movement. As heretofore described, the material for elastomeric cushion 128 can vary depending on the desired range of movement for the individual patient. Elastomeric cushion 128 is formed of material to provide a range of movement that is anticipated for the specific patient by taking into consideration the anticipated range of movement of the natural tooth, and it will preferably provide a range of movement between about 0.1 mm and about 2.5 mm. One skilled in the art could use tools, such as the Miller Index or a paradontometer, to measure and assess the anticipated range of movement for natural tooth 112 when selecting the material, shape, and size of elastomeric cushion 128. Elastomeric cushion 128 may be made from a combination of materials and may also have layers or zones of different materials. Examples of suitable materials include but are not limited to rubber, silicone, nylon, polyethylene, copolymers, plastic, Teflon®, compomers, elastomers, santoprene, high density polyethylene, cross-linked polyethylene, polyoxymethelene, other biocompatible materials, and combinations thereof.

From the foregoing it will be seen that this invention is one well adapted to attain all ends and objectives herein-above set forth, together with the other advantages which are obvious and which are inherent to the invention.

Since many possible embodiments may be made of the invention without departing from the scope thereof, it is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. For example, while the elastomeric cushion is shown in direct contact with the surfaces of the prosthesis and implant components, it is anticipated that the cushion may be positioned in indirect contact with these components without departing from the scope of the invention. Further, it will be understood that certain features and subcombinations are of utility and may be employed without reference to other features and subcombinations. This is contemplated by and is within the scope of the claims.

What is claimed and desired to be secured by Letters Patent is as follows:

1. A dental bridge system for connecting a natural tooth to a dental implant, said system comprising:
    a dental prosthesis having a tooth crown comprising a cap structure configured to be semi-permanently fixed to a natural tooth and having a key received within a portion of a dental implant, wherein said key has bottom and side surfaces that interface with the portion of the dental implant; and
    an elastomeric cushion positioned between the dental implant and said bottom and side surfaces of said key, said elastomeric cushion configured and positioned such that said dental prosthesis and said dental implant do not directly contact one another and such that said elastomeric cushion permits a range of movement of said dental prosthesis relative to the dental implant in response to on-going movement of the natural tooth from time to time during use of the dental bridge system, wherein said range of movement corresponds with the anticipated range of movement of the natural tooth during use of the dental bridge system and is between 0.1 mm and about 2.5 mm.

2. The system according to claim 1 wherein said elastomeric cushion is fixed to said key.

3. The system according to claim 1 wherein said elastomeric cushion is made from more than one material.

4. The system according to claim 3 wherein said elastomeric cushion further comprises zones of said more than one material.

5. The system according to claim 1 wherein said elastomeric cushion is configured and positioned to permit said dental prosthesis to move at least about 0.25 mm relative to the dental implant.

6. The system according to claim 1 wherein said key further comprises a horizontal extension and a vertical arm.

7. The system according to claim 1 wherein said key further comprises a bulbous distal end.

8. The system according to claim 1 wherein said dental prosthesis further comprises at least one pontic between said tooth crown and said key.

9. A dental bridge system comprising:
    a dental prosthesis having a tooth crown comprising a cap structure configured to be semi-permanently fixed to a natural tooth and having a key;
    a dental implant having a notch that receives said key; and
    an elastomeric cushion positioned between said key and said dental implant, said elastomeric cushion configured and positioned such that said dental prosthesis and said dental implant do not directly contact one another and such that said elastomeric cushion permits a range of movement of said dental prosthesis relative to said dental implant in response to on-going movement of the natural tooth from time to time during use of the dental bridge system, wherein said range of movement corresponds with the anticipated range of movement of the natural tooth during use of the dental bridge system and is between 0.1 mm and about 2.5 mm.

10. The system according to claim 9 wherein said dental implant further comprises an exposed portion and an implant crown, and wherein said notch extends into said implant crown and said exposed portion.

11. The system according to claim 9 wherein said elastomeric cushion is fixed in said notch.

12. The system according to claim 9 wherein said notch holds said elastomeric cushion in place by an interference fit.

13. The system according to claim 9 wherein said elastomeric cushion is fixed to said key.

14. The system according to claim 9 wherein said elastomeric cushion is made from more than one material.

15. The system according to claim 14 wherein said elastomeric cushion further comprises zones of said more than one material.

16. The system according to claim 9 wherein said elastomeric cushion permits said dental prosthesis to move at least about 0.25 mm relative to said dental implant.

17. The system according to claim 9 wherein said key further comprises a horizontal extension and a vertical arm.

18. The system according to claim 9 wherein said key further comprises a bulbous distal end.

19. The system according to claim 9 wherein said dental prosthesis further comprises at least one pontic between said tooth crown and said key.

* * * * *